United States Patent [19]

Tsuchida et al.

[11] 4,000,040
[45] Dec. 28, 1976

[54] METHOD FOR PRODUCING L-ASPARTIC ACID BY FERMENTATION

[75] Inventors: Takayasu Tsuchida; Koji Kubota, both of Kawasaki; Yoshio Hirose, Fujisawa, all of Japan

[73] Assignee: Ajinomoto Co., Inc., Tokyo, Japan

[22] Filed: Nov. 17, 1975

[21] Appl. No.: 632,839

[30] Foreign Application Priority Data

Nov. 22, 1974 Japan ............................ 49-134878

[52] U.S. Cl. ................................... 195/47; 195/29; 195/30; 195/49; 195/79; 195/112
[51] Int. Cl.² ......................................... C12D 13/06
[58] Field of Search ................... 195/65, 30, 47, 42, 195/79, 96, 112, 29, 49

[56] References Cited

UNITED STATES PATENTS

| 3,071,518 | 1/1963 | Scherr et al. | 195/76 X |
|---|---|---|---|
| 3,198,712 | 8/1965 | Takahashi et al. | 195/29 X |
| 3,298,923 | 1/1967 | Banno et al. | 195/112 X |

OTHER PUBLICATIONS

Murgov et al., "Auxotropic Mutants of Brevibacterium Flavum", *Chemical Abstracts*, vol. 79, No. 13, p. 534, Abs. No. 79153e (1973).
Leavitt et al., "Amino Acid–producing Microorganism Mutants", *Chemical Abstracts*, vol. 78, No. 19, p. 335, Abs. No. 122655y (1973).
Oki et al., "Amino Acids by Fermentation", *Chemical Abstracts*, vol. 76, No. p. 317, Abs. No. 84523c (1972).
Kimura et al., "Manufacture of L-Aspartic Acid", *Chemical Abstracts*, vol. 66, No. p. 5108, Abs. No. 54268z (1967).

*Primary Examiner*—A. Louis Monacell
*Assistant Examiner*—Thomas G. Wiseman
*Attorney, Agent, or Firm*—Oblon, Fisher, Spivak, McClelland & Maier

[57] ABSTRACT

L-Aspartic acid is produced by culturing an L-aspartic acid producing mutant strain which is resistant to 6-(dimethylamino)-purine and which is derived from a parent strain belonging to the genus Brevibacterium or Corynebacterium in an aqueous culture medium and then recovering the L-aspartic acid which accumulates in the aqueous culture medium.

6 Claims, No Drawings

METHOD FOR PRODUCING L-ASPARTIC ACID BY FERMENTATION

This invention relates to a method for producing L-aspartic acid by fermentation.

As regards biochemical processes of L-aspartic acid production, L-aspartic acid has been produced from fumaric acid by transamination with the enzymes of bacteria. It is also known that small amounts of L-aspartic acid are produced from hydrocarbons or ethanol by culturing a wild strain of the genus Brevibacterium or Corynebacterium in a suitable medium (Japanese Patent Publication Nos. 879/1965 and 29/1972).

It has now been found that a mutant derived from a microorganism which belongs to the genus Brevibacterium and the genus Corynebacterium and which is resistant to 6-(dimethylamino)-purine which suppresses the growth of the parent strain is especially effective for the production of L-aspartic acid.

The microorganism of this invention belongs to the genus of Brevibacterium and Corynebacterium, and is a mutant resistant to 6-(dimethylamino)-purine.

The mutation is carried out by conventional techniques, for example by exposure of the parent strain to ultra-violet light, X-rays or gamma rays, or to chemical mutagenic agents. The mutant resistant to 6-(dimethylamino)-purine can be selected from the exposed strains by culturing the exposed strains in a medium which contains an amount of 6-(dimethylamino)-purine which suppresses the growth of the parent strain. In the culturing of the exposed strains, the mutant strain preferentially grows over the non-mutant strains and thereafter is isolated.

The best L-aspartic acid producing mutants known to us at this time are listed below with their accession numbers (FERM-P) accorded by the Fermentation Research Institute, Agency of Industrial Science and Technology, at Inage, Chiba-shi, Japan:

Brevibacterium flavum AJ 3859 (FERM-P 2799)
(parent strain: Brev. flavum ATCC 14067)
Brevibacterium lactofermentum AJ 3860 (FERM-P 2800)
(parent strain: Brev. lactofermentum ATCC 13869)
Corynebacterium acetoacidophilum AJ 3877 (FERM-P 2803)
(parent strain: Coryn. acetoacidophilum ATCC 13870)
Corynebacterium glutamicum (Micrococcus geritamicus) AJ 3876 (FERM-P 2802)
(parent strain: Coryn. glutamicum (Micrococcus glutamicus) ATCC 13032)

The foregoing strains are available from the Fermentation Research Institute.

The culture media are conventional, and contain a carbon source, a nitrogen source, inorganic ions, and when required minor organic nutrients.

Suitable carbon sources include carbohydrates such as glucose and sucrose, alcohols such as ethanol, and organic acids such as acetic acid. As the nitrogen source gaseous or aqueous ammonia, ammonium ions, and urea are preferably used. As the minor organic nutrients, preferably 2 to 8 $\mu$g/l of biotin is added to the culture medium.

Especially in the cases when the medium contains excessive amounts of biotin, the addition of antibiotics, surfactants, and anti-oxidants to the culture medium increases the yield of L-aspartic acid.

Cultivation is carried out aerobically at 24° to 37° C for 2 to 7 days. During the cultivation, the pH of the medium is adjusted to 5 to 9 with an organic or inorganic acid or alkali, or with urea, calcium carbonate, or gaseous ammonia.

The aspartic acid which accumulates in the culture broth can be recovered by any conventional manner, for example using ion exchange chromatography.

L-Asparic acid in the culture broth was determined by bio-assay method using Leuconostoc mesentroides ATCC 8042.

EXAMPLE 1

Brevibacterium flavum ATCC 14067 was cultured in 5 ml of a medium consisted of 1 g/dl yeast extract, 1 g/dl peptone, 0.5 g/dl NaCl, and 0.5 g/dl glucose (pH 7.0), and cultured at 31° C for 16 hours.

Cells thus obtained were suspended in 5 ml of a phosphate buffer containing 250 $\mu$g/ml N-methyl-N'-nitro-N-nitrosoguanidine, and the suspension was held at 31° C for 30 minutes with stirring. Subsequently cells were recovered from the suspension and washed twice with the phosphate-buffer, and spread on a plate-medium containing 1,000 $\mu$g/ml 6-(dimethylamino)-purine, 2 g/dl glucose, 1 g/dl ammonium sulfate, 0.1 g/dl $KH_2PO_4$, 0.04 g/dl $MgSO_4.7H_2O$, 0.2 mg/dl ferrous ions, 0.2 mg/dl manganese ions, 5.0 $\mu$g/dl biotin, 10.0 $\mu$g/dl thiamine.HCl, and 0.2 g/dl urea, (pH 7.0).

Strains grown on the plate-medium were picked up, and the most effective L-aspartic acid-producer AJ 3859 was selected by culturing the strain in the same manner shown in Example 2, AJ 3859 and ATCC 14067 were cultured on Medium A at 31.5° C for 24 hours, and cells grown on Medium A were suspended in Basal-medium B.

The suspension (0.1 ml) was inoculated in 3 ml of Basal-medium B additionally containing the amount of 6-(dimethylamino)-purine shown in Table 1. Growth was determined after culturing at 31.5° C for 24 hours.

Medium A : 1 g/dl yeast extract, 1 g/dl peptone, 0.5 g/dl NaCl, and 0.5 g/dl glucose.

Basal-medium B : 2 g/dl glucose, 1 g/dl $(NH_4)_2SO_4$, 0.1 g/dl $KH_2PO_4$, 0.04 g/dl $MgSO_4.7H_2O$, 0.2 mg/dl ferrous ions, 0.2 mg/dl manganese ions, 5.0 $\mu$g/dl biotin, 10.0 $\mu$g/dl thiamine.HCl and 3 g/dl $CaCO_3$. (pH 7.0 (KOH)).

Table 1

| 6-(dimethylamino)-purine $\mu$g/ml | Relative growth (%) | |
|---|---|---|
| | ATCC 14067 | AJ 3859 |
| 0 | 100 | 100 |
| 200 | 100 | 98 |
| 400 | 80 | 100 |
| 600 | 60 | 100 |
| 800 | 20 | 95 |
| 1,000 | 0 | 90 |

AJ 3860, AJ 3876 and AJ 3877 were obtained in a manner analogous to that mentioned above. Those strains were more resistant to 6-(dimethylamino)-purine than the parent strain.

EXAMPLE 2

An aqueous culture medium was prepared to contain, per deciliter, 10 g glucose, 7 g $(NH_4)_2SO_4$, 0.25 g $KH_2PO_4$, 0.2 g $MgSO_4.7H_2O$, 0.4 $\mu$g biotin, 35.0 $\mu$g thiamine.HCl, 0.2 mg ferrous ions, 0.2 mg manganese ions, 1 ml soy-protein hydrolyzate ("Mieki") and 5 g calcium carbonate.

300 Ml batches of the aqueous culture medium were placed in 1 l - fermentors, and inoculated with each microorganism listed in Table 2, which was previously cultured on bouillon-slant at 30° C for 24 hours. Cultivation was carried out aerobically at 31° C for 48 hours.

The amount of L-aspartic acid shown in Table 2 accumulated in the resultant culture broths.

A one liter amount of the culture broth of AJ 3859 was passed through a cation-exchange resin ($H^+$). The L-aspartic acid which adsorbed on the resin was eluted with ammonia water, and the eluate was adjusted to pH 2.8. Upon cooling, 6.05 g crystals of L-aspartic acid were obtained.

Table 2

|  | L-Aspartic acid accumulated (g/dl) |
| --- | --- |
| ATCC 14067 | 0.01 |
| AJ 3859 | 1.00 |
| AJ 3860 | 0.73 |
| AJ 3876 | 0.85 |
| AJ 3877 | 0.95 |

EXAMPLE 3

*Brevibacterium flavum* AJ 3859 or *Corynebacterium glutamicum* AJ 3876 was cultured in the seed culture medium mentioned below at 31.5° C for 12 hours:

Seed culture medium:

3.0 g/dl glucose, 0.3 g/dl ammonium acetate, 0.15 g/dl $KH_2PO_4$, 0.04 g/dl $MgSO_4.7H_2O$, 0.2 mg ferrous ions, 0.2 mg manganese ions, 3 ml soy-protein hydrolyzate ("Mieki"), 0.5 μg biotin, 35.0 μg thiamine.HCl, and 0.2 g/dl urea, (pH 8.0).

Two 300 ml batches of the culture medium mentioned below were placed in 1 l-fermentors, and heated with steam. Each batch of the culture medium was inoculated with 15 ml of the seed culture broth mentioned above, and held at 31° C with agitating at 1,350 r.p.m. and aerating at 0.5 vol/vol.min.

Culture medium:

0.8 g/dl ammonium acetate, 0.41 g/dl sodium acetate, 0.30 g/dl $KH_2PO_4$, 0.04 g/dl $MgSO_4.7H_2O$, 0.2 mg/dl ferrous ions, 0.2 mg/dl manganese ions, 2 ml/dl soy-protein hydrolyzate ("Mieki"), 0.5 μg/dl biotin, 10.0 μg/dl thiamine.HCl, and 0.2 g/dl urea, (pH 7.2).

Acetic acid solution (60 %) and gaseous ammonia were fed to the culture medium so as to maintain the pH of the medium at 7.0 to 8.0.

After 48 hours of the cultivation, AJ 3859 consumed 18 g acetic acid per 100 ml medium and produced 2.00 g/dl L-aspartic acid. While, AJ 3876 consumed 20 g acetic acid per 100 ml medium and produced 1.85 g/dl L-aspartic acid.

EXAMPLE 4

*Brevibacterium flavum* AJ 3859 or *Corynebacterium glutamicum* AJ 3876 was cultured in the seed culture medium mentioned below, at 30° C for 18 hours:

Seed culture medium:

3 g/dl glucose, 0.1 g/dl $KH_2PO_4$, 0.04 g/dl $MgSO_4.7H_2O$, 0.2 mg/dl ferrous ions, 0.2 mg/dl manganese ions, 3 ml/dl soy-protein hydrolyzate ("Mieki"), 0.5 μg/dl biotin, 30.0 μg/dl thiamine.HCl, and 0.3 g/dl urea, (pH 7.2).

Two 300 ml batches of the culture medium mentioned below were placed in 1 l fermentors, heated with steam, inoculated with 15 ml of the seed culture broth mentioned above, and held at 31° C with agitation at 1,500 r.p.m, and aeration at 1 vol/vol.min.

Culture medium:

1.5 g/dl ethyl alcohol, 0.5 g/dl $(NH_4)_2SO_4$, 0.1 g/dl $KH_2PO_4$, 0.04 g/dl $MgSO_4.7H_2O$, 0.2 mg/dl ferrous ions, 2 ml/dl soy-protein hydrolyzate ("Mieki") 20.0 μg/dl biotin, 30.0 μg/dl thiamine.HCl, (pH 7.2).

During the cultivation, the pH of the medium was maintained at 7.0 to 7.5 with gaseous ammonia. The concentration of ethyl alcohol in the culture medium was determined by gas-chromatography, and maintained at about 0.1 g/dl.

After 48 hours cultivation, *Brevibacterium flavum* AJ 3859 resulted in the accumulation of 1.30 g/dl L-aspartic acid in the culture broth. From 1 liter of the culture broth, 6.25 g crystals of L-aspartic acid was obtained in a manner analogous to that in Example 1.

On the other hand, *Corynebacterium glutamicum* AJ 3876 resulted in the formation of 1.25 g/dl L-aspartic acid in the culture broth.

What is claimed is:

1. A method for producing L-aspartic acid, which comprises:
   culturing an L-aspartic acid producing mutant strain which is resistant to 6-(dimethylamino)-purine and which is derived from a parent strain belonging to the genus *Brevibacterium* or *Corynebacterium* in an aqueous culture medium; and recovering L-aspartic acid which accumulates in the aqueous culture medium.

2. A method as set forth in claim 1, wherein said parent strain belongs to the genus *Brevibacterium*.

3. A method as set forth in claim 1, wherein said parent strain belongs to the genus *Corynebacterium*.

4. A method as set forth in claim 1, wherein said parent strain belongs to the species *Brevibacterium flavum*, *Brevibacterium lactofermentum*, *Corynebacterium acetoacidophilum*, or *Corynebacterium glutamicum*.

5. A method as set forth in claim 1, wherein said mutant is *Brevibacterium flavum* FERM-P 2799, *Brevibacterium lactofermentum* FERM-P 2800, *Corynebacterium acetoacidophilum* FERM-P 2803, or *Corynebacterium glutamicum* FERM-P 2802.

6. A method as set forth in claim 1, wherein said mutant is cultured in an aqueous culture medium containing as the carbon source carbohydrates, acetic acid or ethyl alcohol.

* * * * *